United States Patent
Skolik et al.

[19]

[11] Patent Number: 5,817,099
[45] Date of Patent: Oct. 6, 1998

[54] UNIVERSAL PORT/SEAL DEVICE FOR OCULAR SURGERY

[76] Inventors: Stephanie A. Skolik, 706 Eleventh Ave., Huntington, W. Va. 25701; John C. Meade, 6 Garfield St., Walpole, Mass. 02081; Kenneth W. Grant, 26 Haven St., Dover, Mass. 02030

[21] Appl. No.: 659,390

[22] Filed: Jun. 6, 1996

[51] Int. Cl.[6] .................................................. A61B 17/00
[52] U.S. Cl. ............................ 606/107; 606/108; 604/22
[58] Field of Search ................................ 606/180, 1, 107, 606/166, 184, 185; 604/164–167, 264, 272, 174, 177, 171, 105

[56] References Cited

U.S. PATENT DOCUMENTS

| | | | |
|---|---|---|---|
| 4,784,138 | 11/1988 | Sinnett | 606/185 |
| 5,122,122 | 6/1992 | Allgood | 604/174 |
| 5,203,773 | 4/1993 | Green . | |
| 5,263,950 | 11/1993 | L'Esperance, Jr. . | |
| 5,330,501 | 7/1994 | Tovey et al. | 604/164 |
| 5,391,156 | 2/1995 | Hildwein et al. | 606/185 |
| 5,490,843 | 2/1996 | Hildwein et al. | 606/185 |

*Primary Examiner*—Wiliam Lewis
*Attorney, Agent, or Firm*—Pandiscio & Pandiscio

[57] ABSTRACT

A universal port/seal device is provided for ocular surgery, notably for cataract surgery. The device is inserted into an ocular incision and is adapted to serve as (1) a port for inserting, manipulating and withdrawing a surgical instrument, e.g., the tip of a phacoemulsification handpiece, so as to protect the surrounding tissue from mechanical and thermal injury, and (2) a seal to prevent leakage of fluid from the eye. The device comprises (1) a housing having an internal passageway that permits it to function as a cannula or port for a surgical instrument, (2) at least two jaws that are movable toward and away from one another and are shaped so as to (a) serve as a seal to prevent leakage from a surgical eye incision and (b) accommodate a surgical instrument or tool that is inserted between them via the housing's internal passageway, and (3) sealing member for preventing leakage of fluid via the housing's internal passageway while allowing relative movement of an inserted surgical device.

42 Claims, 8 Drawing Sheets

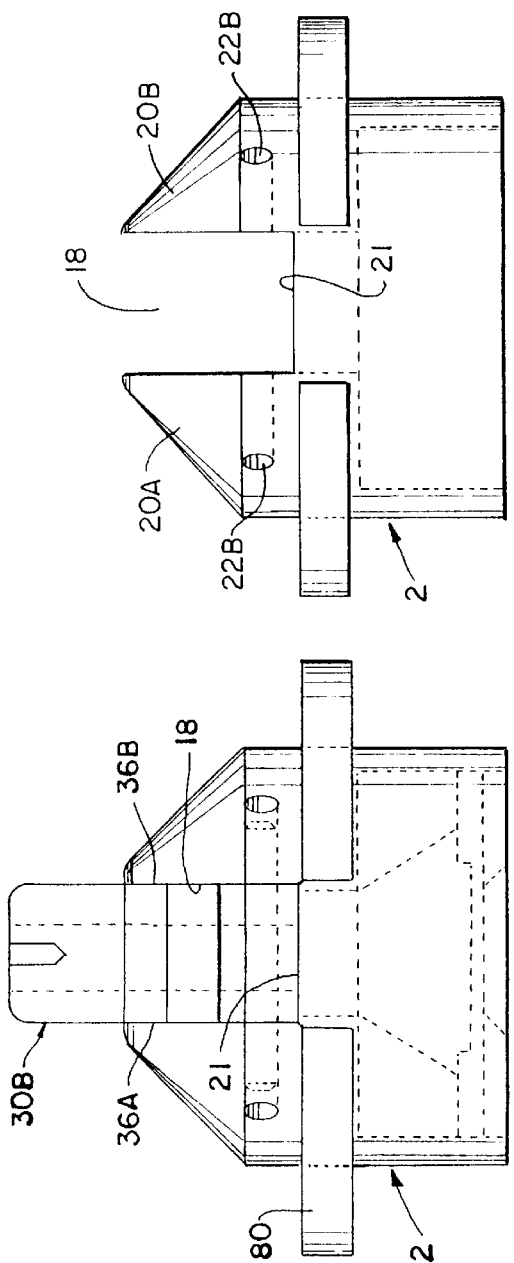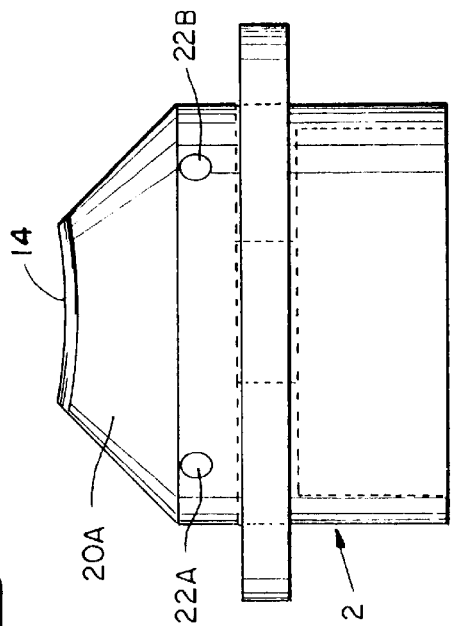
FIG. 5
FIG. 6
FIG. 7

UNIVERSAL PORT/SEAL DEVICE FOR OCULAR SURGERY

This invention relates to cataract surgery utilizing phacoemulsification and more particularly to a universal device for ocular surgery that is placed in the eye once an incision has been made and is adapted to serve as (1) an entry port for the tip of a phacoemulsification handpiece or another surgical device, (2) a seal to prevent leakage of fluid from the eye, and (3) an insulation device to help protect the wound from thermal and/or mechanical injury.

BACKGROUND OF THE INVENTION

The human eye is divided by a normally transparent lens into anterior and posterior chambers. The transparent lens focuses light onto the retina lining the inner surface of the rear posterior chamber. For various reasons, including age and disease, the lens may become cloudy or otherwise deteriorate to the extent of failing to function normally. A typical age-related deterioration problem is the clouding phenomenon commonly known as a "cataract", which inhibits the transmission of visual light information through the lens to the retina. When this happens, the cloudy cataracteous lens material is usually removed if restoration of the maximum light transmission is desired. Thereafter the function of the removed lens material is performed by an intraocular lens ("IOL") implant or by using thick glasses or contact lenses.

A currently accepted practice for removing a cataract through a surgical incision involves a method known as phacoemulsification using ultrasonic energy. This method is preferred since the incision in the eye can be smaller than with some other cataract removal techniques. As currently practiced, the phacoemulsification technique involves use of an electrically-powered "phaco" handpiece or instrument that serves to provide phacoemulsification, irrigation and aspiration. A typical phaco handpiece comprises an acoustic wave-generating transducer that is adapted to conduct ultrasonic energy to the eye via a thin-walled (e.g., 0.250 mm) hollow metal needle or tip. The typical phaco needle is made of titanium and has a length in the order of 24 mm and an outside diameter (o.d.) of about 1 mm. The transducer converts electrical current into acoustic waves with a frequency well beyond the range of human hearing (normally 16,000 cps). Typically the transducer provides an ultrasonic output at a frequency of 28,000 to 50,000 cycles per second. This ultrasonic energy causes the phaco tip to vibrate. The ultrasonic vibrations transmitted to the tip cause the nearby cataracteous tissue to erode and fragment.

Unfortunately mechanical damage or trauma can be caused by the insertion or removal of the phaco tip or other surgical devices at the incision site or along the tunnel of the incision. Also unfortunate is that a portion of the applied ultrasonic energy is converted to heat which is conducted into the eye where it has potential for thermal damage ("thermal burning") to anterior segment tissue. Accordingly a constant flow of a suitable infusion fluid needs to be provided around the shaft of the phaco needle into and out of the anterior segment for the purpose of transferring heat out of the eye and also to remove lens debris (fragmented cataracteous tissue) to permit an unobstructed view of the surgical site. This is achieved by gravity assisted back-pressure sensitive infusion of a selected fluid by means of an infusion sleeve or tube that is mounted in a surrounding relationship with the phaco needle or tip. Usually the infusion sleeve is removable and disposable separate from the needle. Additionally the interior passageway or lumen of the phaco needle or tip is connected by a suitable tube to a hydraulic aspirating pump, whereby pulverized cataracteous material and infusion solution is carried out of the eye. Typically a balanced salt solution is used as the infusion liquid, but other solutions also may be used.

Infusing a fluid into the eye during cataract surgery is important for another reason—namely, to maintain the eye in an inflated, pressurized condition during cataract removal. Nevertheless a common occurrence during cataract surgery is diminished inflation of the eye because of leakage of fluid from the eye. This leakage normally occurs between the edges of the incision and the exterior surface of the infusion sleeve. Such leakage can have adverse consequences on the person being operated on.

A typical adverse consequence of such fluid leakage is the collapse of certain tissues within the eye upon each other or upon a surgical instrument that is in contact with the eye. The tissues which are most likely to be injured from the fluid leakage are the cornea, the iris and the lens capsule, all of which surround the cataract. The fragile cells which line the inside of the cornea are known as corneal endothelium and they cannot be regenerated, i.e., any damage to those cells cannot be repaired. Damage to the corneal enthothelium can result in permanent corneal clouding and decreased vision, which in turn may necessitate a corneal transplant. In this connection, it should be noted that one of the most common causes of corneal clouding and or corneal transplantation in the United States today are complications from eye surgery during the removal of a cataract and/or insertion of an intraocular lens.

Accordingly it is recognized that it would be advantageous, at least from the standpoint of preventing corneal and endothelial damage, to eliminate or minimize leakage of fluid during intraocular surgery. With respect to the leakage problem, it is to be appreciated that in cataract removal procedures, the incision may be straight or curved and is frequently stepped to facilitate wound self-healing when surgery is completed. The incised eye tissue is opened, i.e., dilated or spread apart, by penetration of the phaco tip and infusion sleeve, and the incision assumes an elliptical or tear-drop shape. Regardless of whether the incision is a straight line or curved cut, leakage tends to occur between the dilated incision and the infusion sleeve, with the leakage being due at least in part from the fact that the exterior configuration of that portion of the phaco instrument that is inserted into the incision is circular in cross-section and hence does not match the ellipsoidal shape assumed by the incised tissue when the incision is opened by penetration of the phaco tip and infusion sleeve.

Initially infusion sleeves were made of a relatively stiff or rigid material so as to prevent them from collapsing against the phaco tip and thereby impeding flow of infusion fluid. However, stiff infusion tubes resulted in the aforementioned leakage problem.

Various efforts have been made to reduce such leakage. Such efforts are exemplified by U.S. Pat. No. 5,084,009, issued 28 Jan. 1992 to Richard J. Mackool for "Fluid Infusion Sleeve For Use During Eye Surgery"; See also Mackool U.S. Pat. Nos. 5,286,256 and 5,354,265, both entitled "Fluid Infusion Sleeve".

FIG. 3 of Mackool's U.S. Pat. No. 5,084,009 discloses the concept of using a rigid metal infusion tube that is ellipsoidal in cross-section so that the tube will more nearly conform to the shape of the expanded incision and thereby eliminate wound leakage. However, that approach has not been satisfactory.

Another known arrangement is to provide the phaco tool with a single infusion sleeve made of a compressible resilient material such a silicone composition. However, use of a single compressible silicone infusion sleeve for a phacoemulsification, irrigation and aspiration handpiece still presents a substantial problem in relation to fluid leakage between the incision and the sleeve and adequate irrigation, and to some extent also in relation to corneal burning. In this connection it is to be appreciated that the size of the incision must be large enough to accommodate the infusion sleeve and avoid compressing the sleeve against the needle, but that is disadvantageous since it tends to worsen the leakage problem. However, when there is a minimal clearance between the exterior of the silicone infusion sleeve and the incised tissue, the non-rigid silicone sleeve tends to be compressed against the vibrating tip, resulting in a relative rubbing movement between the silicone sleeve and the tip that generates heat, which is undesirable since it can result in thermal burns and shrinkage of ocular tissue. Compression of the infusion sleeve against the vibrating needle also tends to constrict infusion fluid flow, thus adversely affecting efforts to keep the eye pressurized and inflated.

A recent development has been to utilize an arrangement such as is shown in FIGS. 5–9 of said U.S. Pat. No. 5,084,009 issued to Mackool, which involves use of two concentric infusion sleeves to improve sealing against leakage while assuring adequate irrigation and aspiration. In this particular embodiment Mackool uses an inner infusion sleeve made of rigid or stiff material such as a metal or Teflon, while the outer sleeve is made of a soft resilient material such as a compressible silicone composition. Other phaco tip/infusion sleeve arrangements also have been developed in an effort to overcome the leakage and irrigation problems described above.

However, even the best designed current phaco tip/infusion sleeve arrangements exhibit some fluid leakage between the incision and the infusion sleeve due to the fact that the outer cross-sectional shape of the infusion sleeve does not closely match the contour of the expanded incision. Although compressible infusion sleeves such as those made of silicone are more easily deformed to an out-of-round shape, there still is a tendency to have fairly substantial gaps between a deformed silicone infusion sleeve and the ends of the incision because the collagen fiber structure of the cornea resists deformity and thus does not readily assume the shape of the infusion sleeve. Those gaps allow fluid to leak out of the eye and give rise to the possibility of tissue damage as noted above.

Complicating the conventional phacoemulsification method of removing cataracteous tissue is the fact that in the course of a surgical procedure the operating instrument may need to be advanced and withdrawn a number of times through the incision. For example, in the course of a cataract removal procedure, the ultrasonic phaco tool may need to be replaced by an irrigation/aspiration handpiece that has no ultrasonic capability.

OBJECTS AND SUMMARY OF THE INVENTION

Therefore, a primary object of the invention is to provide a new and improved device for use in performing cataract and other ophthalmic surgery that facilitates insertion, withdrawal and manipulation of surgical instruments in a manner that protects incised tissue from mechanical or thermal injury by those instruments, and also reduces fluid leakage from the incision.

A further object is to provide a new device for ophthalmic surgery that serves the dual functions of sealing off an incision and providing a port for the insertion and withdrawal of a surgical instrument through the incision.

Another object is to provide a device for use in cataract surgery that is designed to protect the sclera and corneal tissue from both mechanical and thermal injury, e.g., "corneal burning", as a consequence of use of a phacoemulsification, irrigation and aspiration instrument or handpiece.

A further object is to provide a device whereby a surgical instrument may be inserted into and withdrawn from an eye incision without loss of fluid and with a reduction in corneal burning.

Still another object is to provide a cannula-like device for insertion in an eye incision that functions both as (1) a port through which a surgical instrument can be inserted, manipulated and withdrawn without causing damage to ocular tissue, and (2) as a seal to prevent leakage of fluid from the eye.

Another object is to provide a combination port/seal device for use in eye surgery that is adapted to be inserted into a corneal or scleral incision so as to substantially eliminate any gaps between it and the surrounding corneal tissue, whereby to substantially prevent leakage of fluid from the incision.

Yet another object of this invention is to provide a novel combination of a phaco surgical instrument and an incision sealing device.

Still another object is to avoid the use of dual infusion sleeves surrounding the needle tip of a phaco surgical instrument and also to eliminate the need to use soft compressible infusion sleeves.

Another object is to provide a device that serves as small incision lens delivery system or pathway for delivering an IOL into the eye.

Yet another object is to provide a novel port/seal device in combination with an installation tool for holding the device and inserting it into an eye incision.

The foregoing, as well as other objects hereinafter described or rendered obvious by the following detailed description of preferred and other embodiments of the invention, are achieved by providing a port/seal device that essentially comprises (1) a housing having an internal passageway that permits it to function as a cannula or port for a surgical instrument, (2) at least two jaws that are movable toward and away from one another and are shaped so as to (a) serve as a seal to prevent leakage from a surgical eye incision and (b) accommodate a surgical instrument or tool that is inserted between them via the housing's internal passageway, and (3) sealing means for preventing leakage of fluid via the housing's internal passageway. For cataract surgery the new seal/port device is used in combination with a phaco instrument having a single, rigid or stiff infusion sleeve surrounding its hollow aspirating needle.

Other features and the attendant advantages of the invention are disclosed in or rendered obvious by the accompanying drawings and the following detailed description of preferred and alternative embodiments.

BRIEF DESCRIPTION OF THE DRAWINGS

FIG. 5 is a side view in elevation of the same preferred embodiment but with the latter rotated 90 degrees from its position in FIG. 1;

FIG. 6 is a side view in elevation of the body of the same embodiment;

FIG. 7 is a side view in elevation of the same body with the latter rotated 90° from the position shown in FIG. 6;

Figure 1:
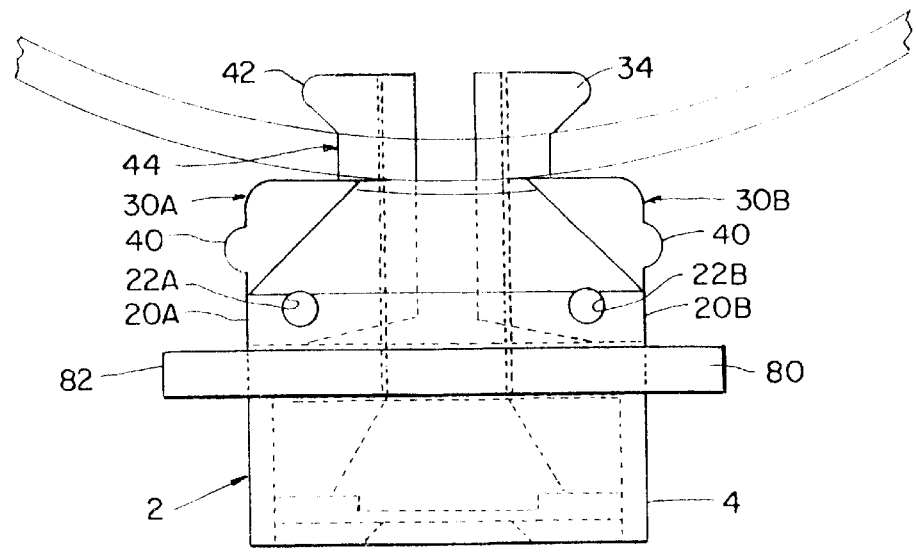
FIG. 1 is a side view in elevation of a preferred embodiment of the invention with the incision-opening jaws in open (separated) position.

In the drawings the relative sizes and proportions of the various components of the illustrated embodiment of the invention are not intended to be limiting; instead the relative sizes of the components may be varied according to what is required to achieve optimum performance. Unless otherwise indicated, the shapes of the various components also may be varied.

DESCRIPTION OF PREFERRED EMBODIMENT OF THE INVENTION

Referring first to FIGS. 1–8, the preferred embodiment comprises a hollow body or housing 2 that preferably is made of a suitable inert and stiff or rigid material, e.g., a plastic such as Teflon® or PMMA or a silicone or a metal such as stainless steel. Housing 2 has a generally cylindrical outer surface 4, and an internal passageway that is characterized by a first bore section 6 of a predetermined diameter and a second bore section 8 with a diameter that is less than that of bore section 6. The internal passageway is intended to permit insertion of a surgical tool at the proximal end of the device, i.e., the bottom end of the device as viewed in FIG. 2.

The distal end of housing 2 is frustoconically shaped (FIGS. 5–7) and preferably its upper or distal end surface 14 has a concave curvature, as seen in FIG. 7. The distal end of the housing also is divided by a diametrically extending slot 18 (FIGS. 3, 5 and 6) so as to form a yoke section that is characterized by two like parallel arms 20A and 20B. Slot 18 also intersects bore section 8. Each of the arms 20A and 20B is formed with a pair of holes 22A and 22B. Holes 22A and 22B of arms 20A are aligned with holes 22A and 22B of arm 20B and serve to accommodate pivot pins 26A and 26B (FIG. 2) that are used to pivotally attach two jaws 30A, 30B to housing 2.

As seen in FIGS. 1–5 and 8, jaws 30A and 30B are identical to one another. Each jaw 30 is characterized by a body portion 32 and a tissue-engaging incision-penetrating portion 34 (FIG. 2) that is an extension of body portion 32. Each body portion 32 has a pair of flat opposite side surfaces 36A and 36B (FIGS. 3, 8) and has a thickness sized to allow it to make a close sliding fit in slot 18 between arms 20A and 20B. The outer end of each body portion 32 has an end surface 38 that forms a shoulder for the jaw. The shoulders 38 of jaws 30A and 30B function as stops to limit the extent to which the jaws can be inserted into the eye via the incised wall of the eye. The body portion 32 of each jaw 30 also has a projection 40 (FIGS. 1, 2) on its outer edge surface whereby it may be engaged to move it into the closed position shown in FIG. 4. The body portion of each jaw 30 also has a hole located adjacent its bottom (proximal) end to accommodate one of the pivot pins 26 A, B.

Figure 2:
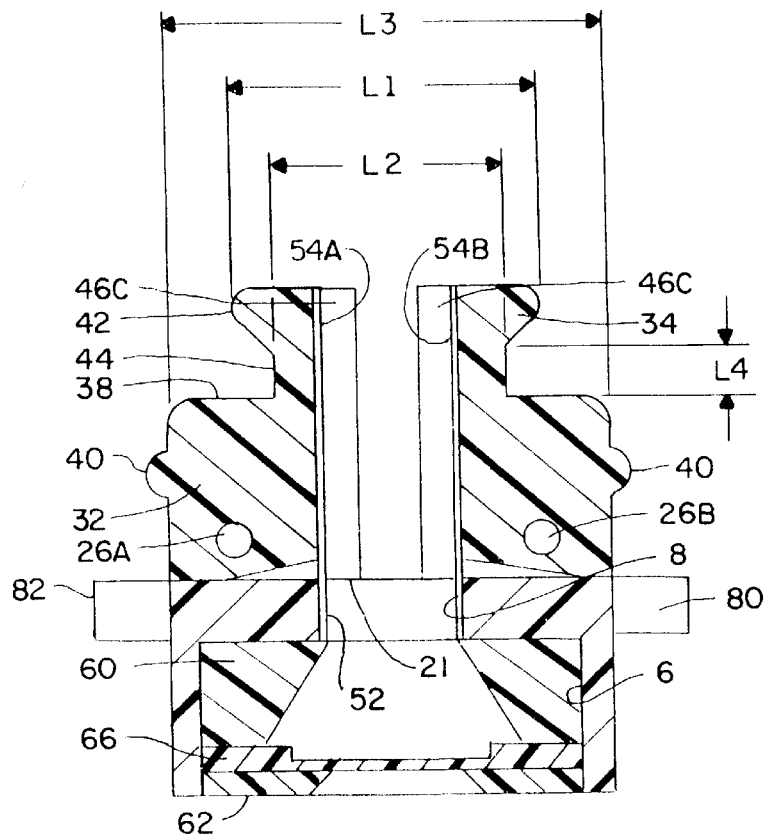
FIG. 2 is a longitudinal sectional view of the same embodiment.
Figure 3:
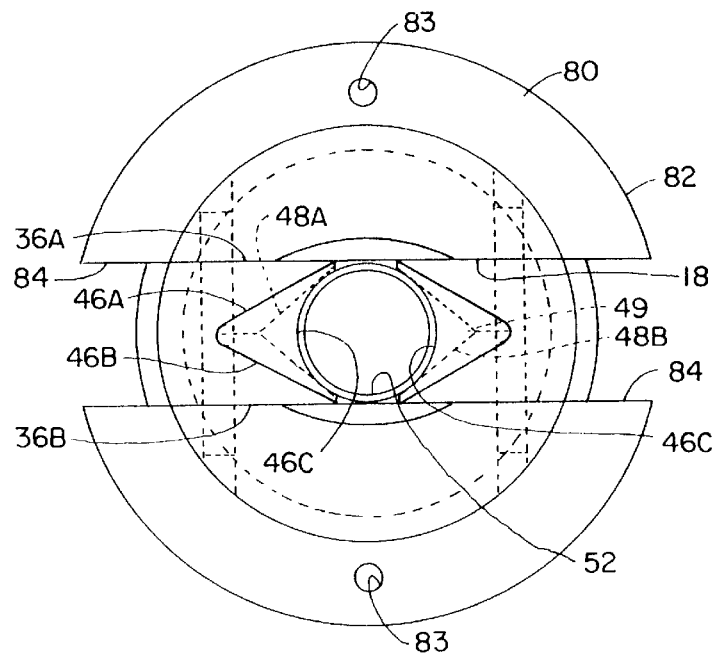
FIG. 3 is a front (distal) end view of the same embodiment with the incision-opening jaws in open position.
Figure 4:
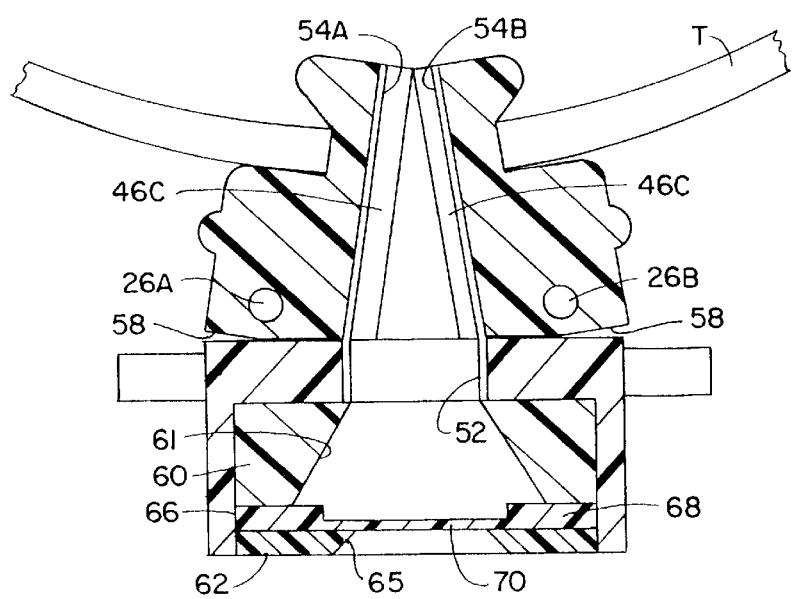
FIG. 4 is a longitudinal section view like FIG. 2 but with the incision-opening jaws in closed position.

Referring now to FIGS. 2 and 4, preferably the incision-penetrating portion 34 of each jaw is stepped, having a relatively large outer (distal) end section 42 and a relatively small inner (proximal) end section 44 that is joined to body portion 32. Each of the sections 42 is shaped so that its outer surfaces form a generally triangular configuration, comprising (as seen best in FIGS. 3 and 8) a pair of mutually-converging longitudinally-extending outer side surface sections 46A and 46B that intersect a curved longitudinally-extending inner side surface section 46C (FIGS. 3 and 4) that extends for the full axial length of the jaws. The outer ends of surface sections 46A and B converge as shown at 47 in FIG. 9. Preferably, but not necessarily, the juncture 47 is rounded off to form a generally blunt tapered corner.

Figure 8:
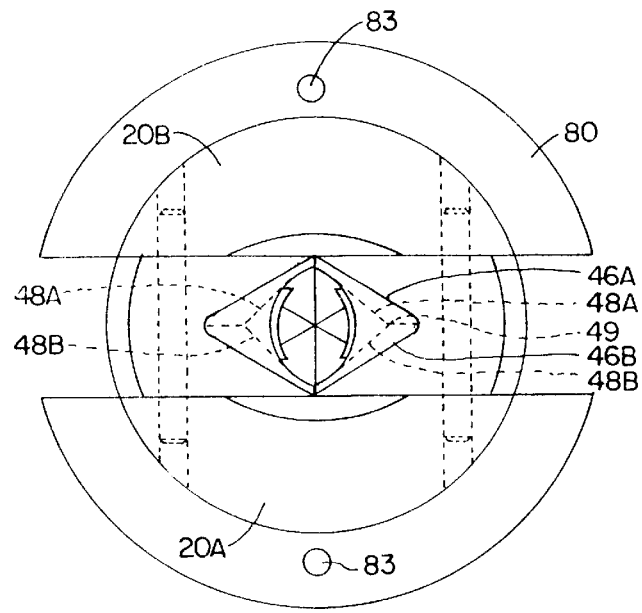
FIG. 8 is a view like FIG. 3 but with the jaws in the closed position of FIG. 4.
Figure 9:
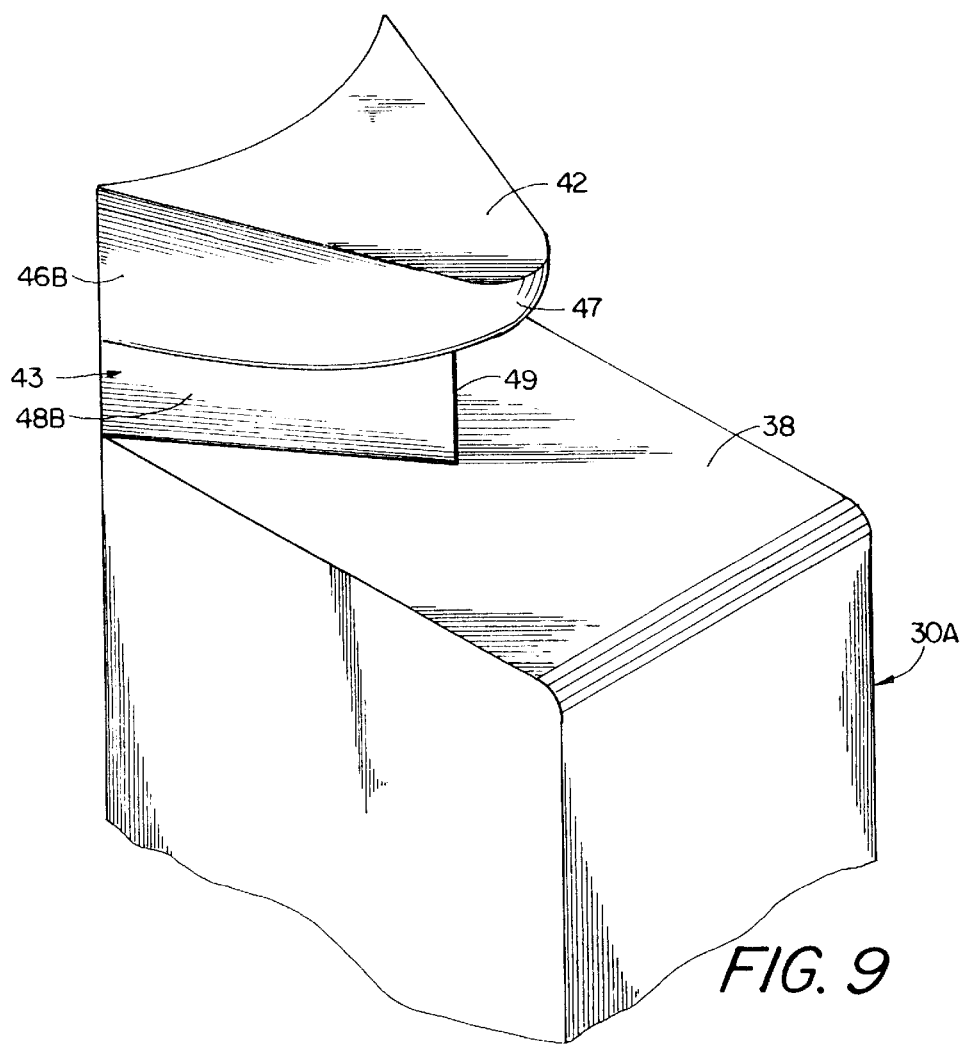
FIG. 9 is an enlarged fragmentary view in perspective of one of the two incision-engaging jaws.
Figure 10:
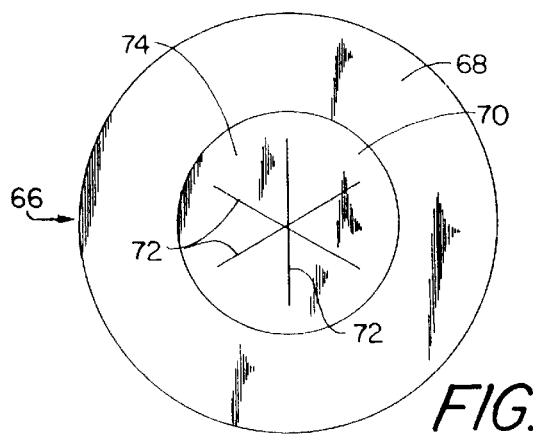
FIG. 10 is a plan view of the sealing member that forms part of the embodiment of FIGS. 1–4.
Figure 11:
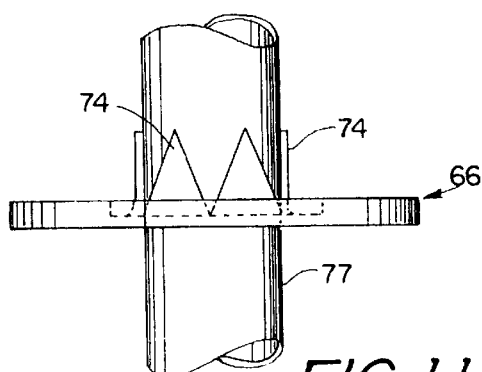
FIG. 11 is a fragmentary elevational view illustrating how the sealing member of FIG. 10 yields to accommodate an inserted instrument.
Figure 15:
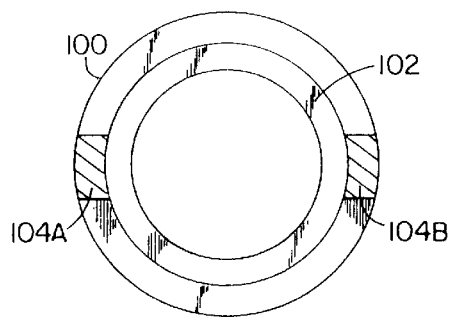
FIGS. 15 and 16 are views taken along lines 15—15 and 16—16 of FIG. 12.
Figure 16:
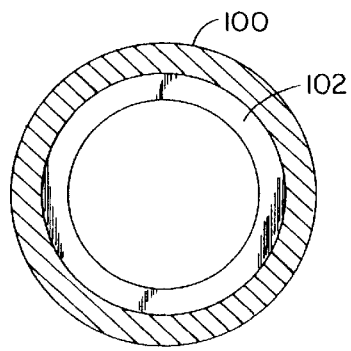

The external shape of each jaw section 44 also is generally triangular. More specifically each proximal end section 44 of each incision-penetrating portion 34 has a pair of mutually-converging longitudinally-extending side surface sections 48A and 48B (FIGS. 3 and 8) that intersect inner surface section 46C. Preferably the juncture of each pair of opposite side surfaces 48A, 48B forms a relatively sharp tapered corner 49 as shown in FIGS. 3, 8 and 9.

Figure 20:
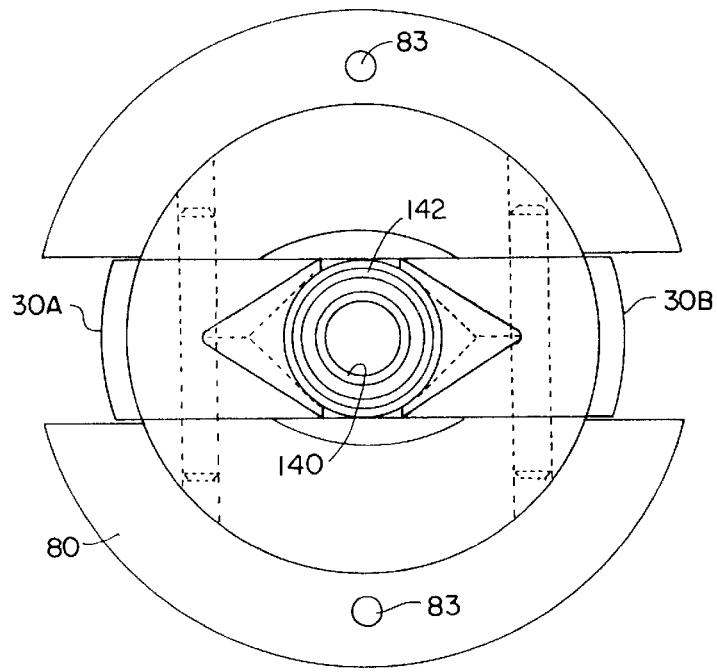
FIG. 20 is an end view similar to FIG. 3 but with a phaco tip and infusion sleeve inserted in the port device.
Figure 19:
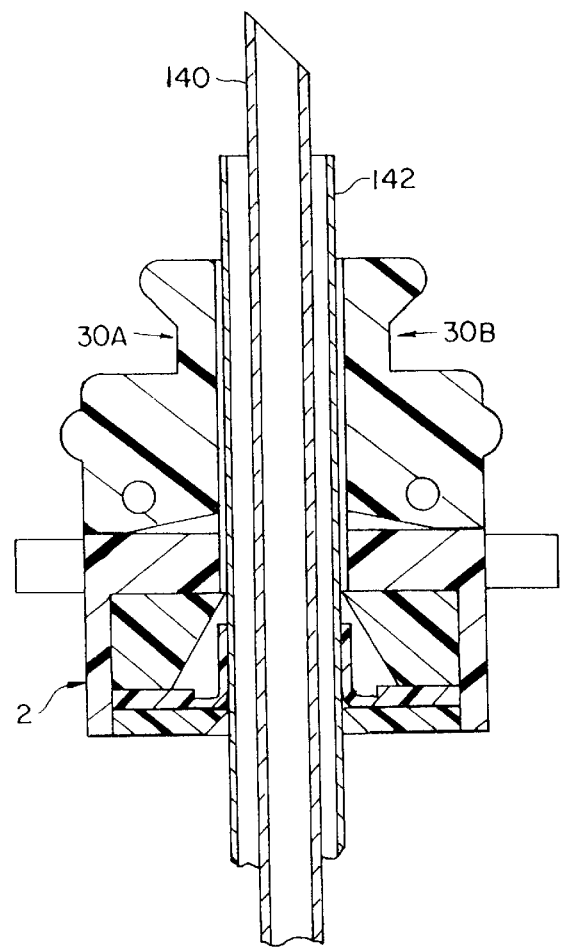
FIG. 19 is a longitudinal sectional view'similar to FIG. 2 but with a phaco tip and infusion sleeve inserted between the incision-opening jaws.

The inner curved surface sections 46C extend for the full length of jaw sections 42 and 44, as shown in FIG. 2, and have a circular curvature in cross-section, each having a radius of curvature such as to cause it to closely embrace a cylindrical infusion tube (as shown in FIGS. 19 and 20) or other surgical instrument. Preferably, the radius of curvature of surface section 46C is the same as that of bore section 8.

As viewed on end or in cross-section, each pair of surface sections 46A, 46B forms a shape conforming generally to one end of an ellipsoid. The same is true of each pair of surface section 48A, 48B. Hence the incision-sealing portions 34 of jaws 30A and 30B, or at least their proximal end sections 44, have an end view or cross-sectional configuration conforming to that of an ellipsoid. Accordingly when the two jaws are extended to open position, their outer surface sections 48A and 48B will conform very closely to the shape of the ends of an expanded eye incision.

Referring now to FIGS. 2–4, the device also includes a short metal sleeve 52, preferably made of a resilient metal such as a stainless steel, that is press fitted in bore 8 and has two diametrically-opposed extensions 54A, 54B that extend up along the inner surfaces 46C of jaws 30A, 30B. Sleeve 52 has a relatively thin wall, preferably a wall thickness of about 0.1 to about 0.12 mm, so that its extensions 54A, 54B have substantial flexibility. The extensions 54A, 54B of sleeve 52 have a width (measured along the circumference of sleeve 52) of about 1.2–1.6 mm, whereby they can function as leaf springs to hold the jaws in the open position shown in FIG. 2.

Articulating movement of jaws 30A and 30B is permitted by anchoring those jaws to arms 20A and 20B by means of pivot pins 26A, 26B (FIG. 4). The pins are locked in arms 20A and 20B by suitable means, e.g., by a friction fit or by means of a suitable bonding agent, e.g., a cement.

The jaws are held by leaf spring sections 54A, 54B in the open position shown in FIG. 2 in the absence of any externally-applied restraining force. Preferably the lower edge surface of each jaw is angulated as shown at 58 in FIG. 4 so as to facilitate pivotal movement and also limit such movement. Opening movement of the jaws is limited by engagement of the outer angulated portions of their lower edge surfaces 58 with the base 21 of slot 18 (FIGS. 2 and 6), while as shown in FIG. 4 closing movement of the jaws is determined by engagement of the inner angulated portions of those lower edge surfaces with base 21. Alternatively the limit of closing movement can be determined by mutual engagement of the inner jaw surface sections 46C.

Referring again to FIGS. 2–4, the device also includes a spacer ring 60, an annular retaining ring or washer 62, and a circular seal member 66. Spacer ring 60 is made of an inert rigid or stiff material, e.g., a plastic or a metal, sized to make a close fit in bore 6 and its inner surface 61 is preferably tapered as shown to facilitate insertion of a surgical instrument between jaws 30A, 30B, with the minimum inner diameter of spacer 60 preferably set so that the spacer will engage the bottom end of sleeve 52 but will not protrude inwardly beyond the inner surface of that sleeve, whereby spacer 60 provides a tapered entrance to sleeve 52 but does not reduce the effective inner diameter of that sleeve. Retainer ring 62 is made of a stiff or rigid material, e.g., a plastic or a metal such as stainless steel. Ring 62 is secured in bore 6, preferably by means of a press fit or by a suitable cement or other bonding agent. The inner diameter of ring 62 is equal to but preferably greater than the minimum inner diameter of spacer 60 and additionally it is preferred but not necessary that the inner edge surface 65 of ring 62 be beveled or tapered as shown to facilitate introduction of a surgical instrument.

Turning now to FIGS. 2, 4, 10 and 11, seal member 66 serves as a means of preventing leakage of fluid from the surgical site via the passageway defined by bore sections 6 and 8, and jaws 30A, 30B. Various forms of fluid-sealing means may be employed, but a sealing member as shown at 66 is preferred. Member 66 is essentially a self-sealing valve, and is elastomeric, being made of a natural or synthetic rubber or a plastic that exhibits elastomeric properties, e.g., a silicone rubber, of selected durometer. It comprises a relatively thick annular rim portion 68 and a central sealing portion 70. The outside diameter of rim portion 68 is sized so that it will make a close fit in bore section 6. The central section 70 has several diametrically extending mutually-intersecting razor-cut slits 72 that define a plurality of distinct wedge-shaped portions 74. Since the seal member is flexible and resilient, the central portion 70 can flex and will part along the slits 72 when an instrument as shown schematically at 77 (FIG. 11) is inserted into the device, with the wedge-shaped portions 74 bending out of the plane of the seal member so as to lie alongside and in engagement with the outer surface of the inserted instrument. The rim portion 68 of seal member 66 is compressed between retaining ring 62 and spacer 60, and that compression causes it to make a fluid-tight seal with the surrounding device body 2. Preferably seal member 66 has a durometer in the range of 35–60 on the A scale, with the result that when no instrument has been inserted into the device, the wedge-shaped portion 74 will tend to remain in co-planar relationship with one another despite the presence of fluid attempting to escape from the eye, whereby the seal member prevents outflow of fluid from the eye. However, because of the selected durometer (and hence stiffness) of seal member 66, when the wedge-shaped portions are bent out of the way by an inserted instrument 77, they will tend to lie tightly against that instrument and thereby form a fluid seal therewith to prevent outflow of fluid from the eye.

With current surgical techniques, it is preferred for cataract surgery that the outer surface of body 2 will have a maximum diameter in the range of about 3.0 to about 6.0 mm, and the overall length of the device (body 2 and jaws 30), i.e., the vertical dimension in FIGS. 1, 2, 4 and 5, will be in the range of about 3.5 to about 7.0 mm. For such a device, it is preferred that the jaws be formed so that the outer surfaces of their body portions 32 will be flush with the outer surface of body 2 when the jaws are in their open position (FIG. 2). Preferably, each of the projections 40 is sized so that it projects beyond the outer surface of body portion 32 by about 0.25–0.40 mm. Hence, each projection 40 will extend beyond the periphery of body 2 by about 0.25–0.40 mm when the jaws are in the open position shown in FIG. 2 and will be flush with, or located inboard of the periphery of body 2, when the jaws are in the closed position shown in FIG. 4. For cataract eye surgery, it is preferred but not required, that the maximum diametral distance at the relatively large end section 42 (the dimension L1 in FIG. 2) is about 4.2 mm, while the maximum diametral distance at the proximal end sections 44 (the dimension L2 in FIG. 2) is about 3.2 mm. Excepting projections 40, for cataract eye surgery the maximum diametral dimension measured between the outer surfaces of jaw body portion 32 (the dimension L3 in FIG. 2) is substantially the same as that of body 2, preferably about 5.5 mm, and the axial dimension of each proximal section 44 (the dimension L4 in FIG. 2) is preferably about 0.75 mm.

Referring again to FIGS. 1–8, the body 2 is provided with a peripheral flange 80 having a cylindrical outer surface 82. Flange 80 is slotted, preferably at two diametrically-opposed points as shown at 84 (FIG. 3). Flange 80 serves to provide the surgeon with a gripping portion whereby the port/seal device may be gripped, e.g., with a suitably-sized forceps, for the purpose of adjusting its position in an eye incision and/or withdrawing it from the incision after the surgical procedure is finished. The slots 84 are provided to facilitate mating of the port/seal device with the installation tool described hereinafter. As an optional measure, flange 80 may be provided with one or more holes 83 whereby a hooked instrument may be used to manipulate the port/seal device.

Figure 17:
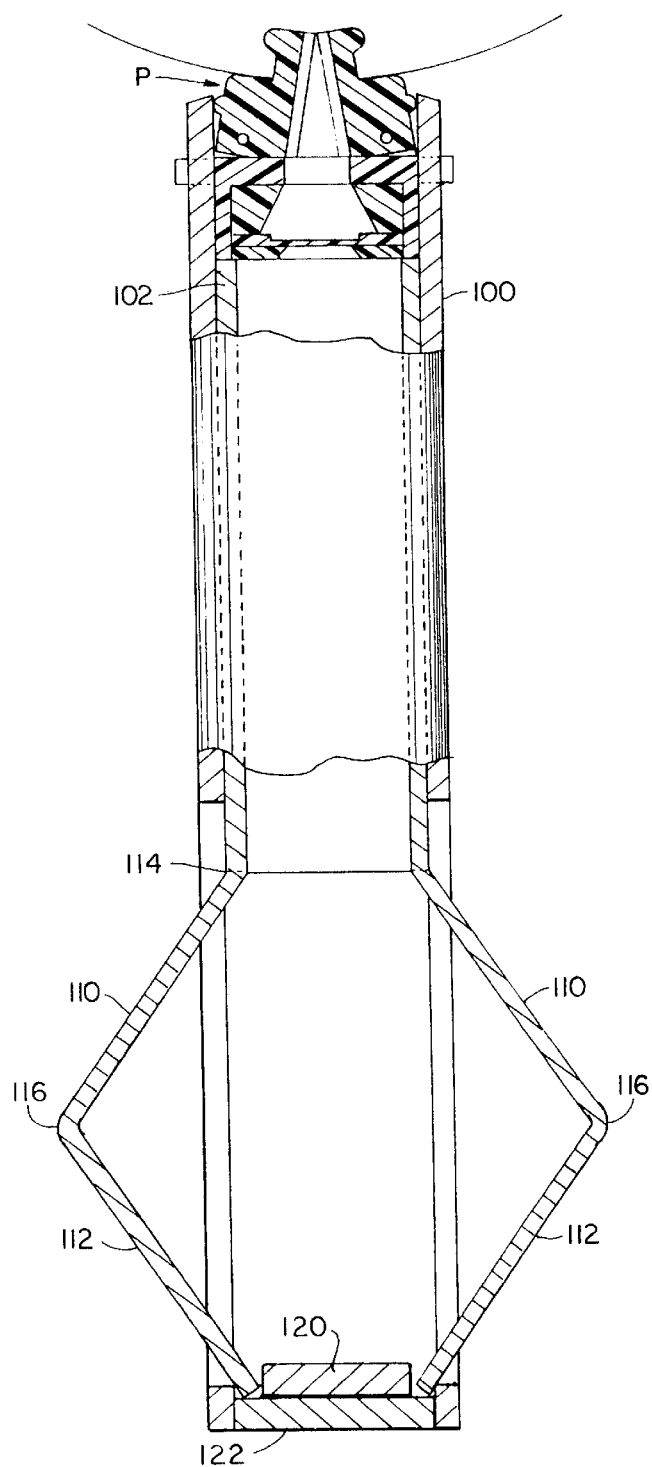
FIGS. 17 and 18 show the device of this invention in association with the installation tool of FIGS. 12–14.
Figure 18:
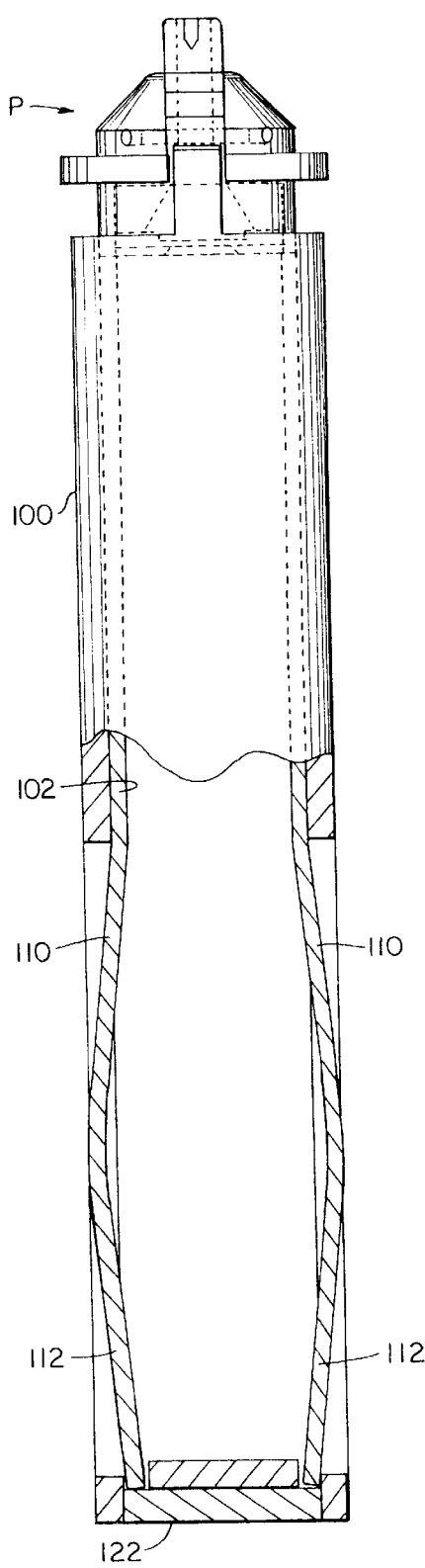

FIGS. 12–16 illustrate an installation tool for holding the port/seal device and inserting it into an eye incision. The tool consists of outer and inner concentric tubes 100 and 102, with inner tube 102 being capable of telescoping movement relative to outer tube 100. Outer tube 100 functions as a handle or handpiece and also as a dispenser-type holder for a port/seal device like the one shown in FIGS. 1–11. The port/seal device, identified as "P" in FIGS. 17 and 18, is inserted into the forward end of outer tube 100, the latter having an inside diameter that is sized so that its inner cylindrical surface accommodates the body of the device and exerts a radially-directed compressive force on projections 40 so as to force jaws 30A and 30B to closed position, as shown in FIG. 17. Tube 100 may be made of an suitable inert material, e.g., stainless steel or a suitable plastics material such as Teflon or polyethylene or polypropylene.

As seen in FIGS. 12–16, the upper or distal end of tube 100 is provided with two diametrically opposed extensions 104A, 104B that are sized to make a close sliding fit with slots 84 of the port/seal device.

Inner tube 102 is preferably made of a resilient plastic material, e.g., polyethylene, and is formed with a two diametrically opposed articulated arms that are disposed in diametrically-opposed slots 108 in tube 100. Each articulated arm consists of a forward arm section 110 and a rearward arm section 112, with arm section 110 being attached at its forward end to the rear end of tube 102 by a living hinge 114 and attached at its rear end to arm section 112 by a second living hinge 116. As is well known, so-called "living hinges" are created by deforming a resilient material, e.g., a plastic material like polyethylene, along a given line so that it can fold along that line. Alternatively, a living hinge may be formed by reducing the thickness of the resilient material along the desired fold line. The rear ends of arm sections 112 are captivated in the rear end of tube 100 by a disk 120 that is attached to an end plug 122 that is secured in the end of tube 100. Disk 120 is sized so that its peripheral surface is spaced from tube 100, and the rear ends of arm sections 112 are captivated in a pivot-like arrangement between the inner surface of tube 100 and the outer surface of disk 120.

Figure 12:
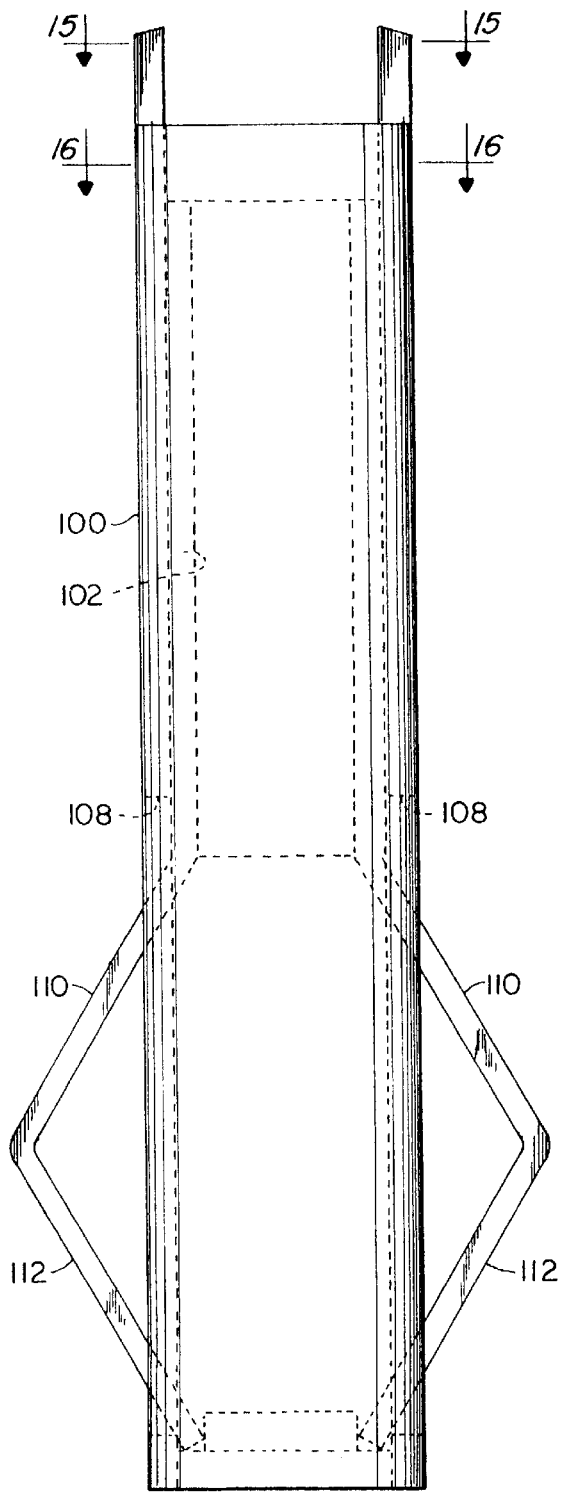
FIGS. 12–14 are side elevations of one form of installation tool for use in deploying port devices made according to this invention.
Figure 13:
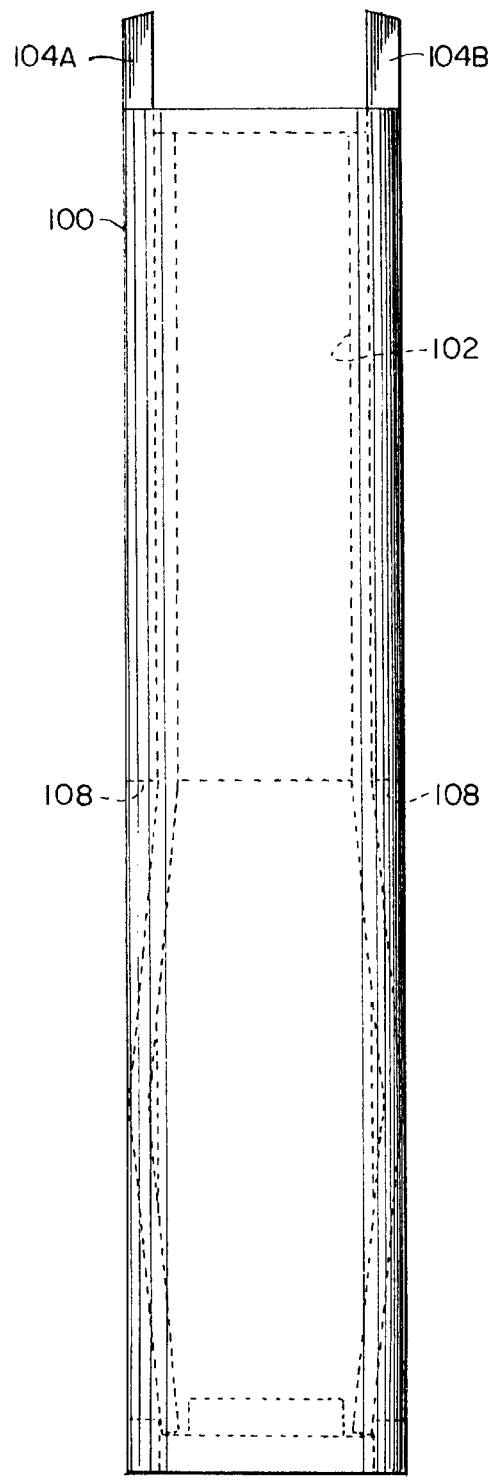
Figure 14:
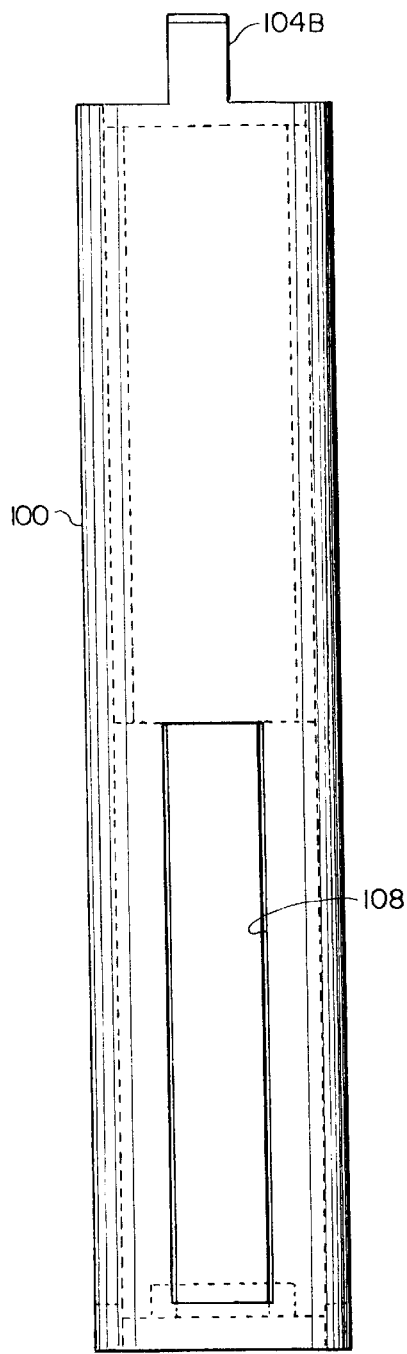

The articulated arms are formed so that normally arm sections 116 are located at a relatively sharp angle to arms sections 112, as shown in FIGS. 12 and 17. When the arms are in that position, the forward end of tube 102 is in retracted position, near to or lightly engaging the rear end of the port/seal device P, with the latter being disposed so that its jaws protrude from tube 100 as shown in FIG. 17. However, because of the living hinges, arms sections 110 and 112 can be manually forced to a less angular relationship, thereby moving inner tube 102 axially in tube 100 so as to force the device P forward far enough to free its jaws 30A, 30B from tube 100, as shown in FIG. 18. Once jaws 30A, 30B are released from tube 100 so as to engage surrounding eye wall tissue T, as shown in FIG. 4, the installation tool can be withdrawn so as to leave the seal/port device P installed in the eye incision.

FIGS. 1 and 4 illustrate schematically at T the wall tissue or sclera of an eye and how the port/seal device of the present invention is positioned in an incision in that tissue. The jaws 30A, 30B are inserted in the eye by means of the installation tool, the jaws being in the retracted position of FIG. 4 when inserted into the incision. The device is inserted far enough to align the jaw portions 44 with the incised tissue, whereupon the installation tool is operated to move the device forward in the tool so as to release its jaws 30A, 30B and cause them to open into engaging relation with the incised tissue T. Once the jaws are engaged with the incised tissue, the installation tool is moved free of the installed port/seal device and thereafter the latter may be used for introduction to the surgical site of the tip and infusion sleeve of a phaco instrument or some other surgical instrument.

It is to be understood that the invention comprises not only the port/seal device shown in FIGS. 1–5, alone and also in combination with an installation tool as shown in FIG. 17, but also the combination of that port/seal device with surgical instruments (e.g., a phaco surgical instrument as described above) that are introduced to the surgical site by means of the sealing device.

Various surgical instruments may be used with the new sealing device. Thus, for example, the surgical instrument may be a phaco handpiece of the type comprising an ultrasonically-vibrated needle and a surrounding infusion sleeve. Alternatively the surgical instrument 77 may comprise a phaco handpiece of the type that is characterized by a laser or which has irrigation and aspiration properties but lacks means such as an ultrasonic or laser generator for disintegrating diseased tissue. Also other surgical instruments commonly used in ocular surgery may be used with the new port/seal device, e.g., forceps, manipulators, and the like.

An important advantage of this invention is that it simplifies the infusion sleeve arrangement of phaco tips used for cataract surgery. The invention eliminates the need to use a soft, compressible infusion sleeve or to use the same together with an inner non-compressible infusion sleeve as taught in said Mackool U.S. Pat. No. 5,084,009. Referring now to FIGS. 19 and 20, this invention embraces and includes the concept of using a phaco instrument comprising a conventional ultrasonically vibratable needle 140 (e.g., a needle having a slanted surface at its front end or tip as shown in FIG. 19) and a single thin-walled infusion sleeve 142 that is thin-walled and made of a rigid or stiff material, e.g., a Teflon, silicone or stainless steel sleeve. Although not shown, it is to be appreciated that sleeve 142 is adapted to be removably attached to the phaco headpiece (not shown), e.g., by a screw-connection, so that it may be replaced at the surgeon's option.

Following is a description of how the new sealing device is used. Assuming that a surgical incision has been made in the eye and that the new port/seal device P is mounted in its installation tool as shown in FIG. 17 so that the jaws 30A, 30b are in their closed position, the installation tool is manipulated so as to insert the jaws 30A, 30B into the incision, with the longest cross-sectional dimension of their incision-sealing portions 34A and 34b being aligned with the incision. The jaws 30A, 30B are inserted far enough for their incision-sealing portions 44 to be surrounded by the incised tissue T. Then the installation tool is operated so as to provide relative movement of the tool and port/seal device so as to release projections 40 from tube 100, whereupon the leaf spring extensions 54A, 54B cause the jaws to pivot to their expanded or open position. In this position the peripheral surfaces 48A, 48B of sealing portions 44 substantially tightly engage the surrounding tissue T that defines the expanded incision, thereby preventing fluid leakage along the region between the incision and the sealing device. Leakage of fluid via the interior of the sealing device is prevented by the sealing means 66. Thereafter a suitable surgical instrument, e.g. a phaco emulsification, irrigation and aspiration tool comprising the hollow untrasonically vibratable needle 140 and the thin-wall stiff or rigid infusion sleeve 142, is inserted into the sealing device. When this is done, sealing means 66 will tightly grip the inserted infusion sleeve and thereby continue to prevent fluid leakage. It should be noted also that the curved inner surfaces 46C of the two jaws (and also the leaf spring extensions 54A, 54B), will substantially fully engage the infusion tube.

Obviously the invention may take forms other than the one specifically described above and illustrated in the drawings. Thus while it is preferred to make the housing and jaws of the device of this invention out of a suitable plastic material such as silicone, Teflon®, PMMA, or propylene that is formulated so as to be rigid or stiff, it is to be understood that those members may be made of other plastic materials or a suitable metal, e.g., stainless steel. Another possible modification is to mold body 2 and jaws 30A, 30B as a single unit.

Also it is contemplated that the housing and/or jaws may be made of a non-rigid semi-soft material. However, using a semi-soft material is not preferred. The important thing is that the device be made out of a material that exhibits the properties most favorable for the intended surgical procedures. Thus it is contemplated that jaws 30 may be made of a resilient material having a durometer such as will permit them to yield under a compressive force to a limited extent necessary to assure contact with the surrounding eye tissue along the entire length of the incision and then to expand to their normal uncompressed state to assure a tight seal with the surrounding tissue.

As noted previously, the sealing means 66 is made of a suitable elastomer or a plastic material that exhibits elastomeric properties, e.g. a synthetic rubber or a resilient plastic such as a silicone or polyethylene. It should be observed also that for some surgical applications it may be desirable to replace or augment the seal member 66 with another different form of sealing device. In this connection it is to be appreciated that prior to this invention, various forms of seals, including sealing valves, have been incorporated into or coupled to surgical cannulas and that persons skilled in the art may elect to use one of those various forms of known seals and sealing valves in practicing this invention.

It also is contemplated that the outer surfaces of jaws 30A, 30B and body 2 may be coated with a friction-reducing material with a smooth texture, e.g., Teflon; to facilitate insertion into and withdrawal from the incision. A further contemplated modification is to impregnate the device with an anti-bacterial compound (bacteriostatic or bactiricidal polymers) to decrease the risk of endophthalmitis. It also is understood that the device may be modified so that one jaw is fixed to the body 2 and the other jaw is pivoted as in the illustrated embodiment. Of course, the materials of which the device is made may be selected according to whether the device is to be reusable or disposable.

Figure 21:
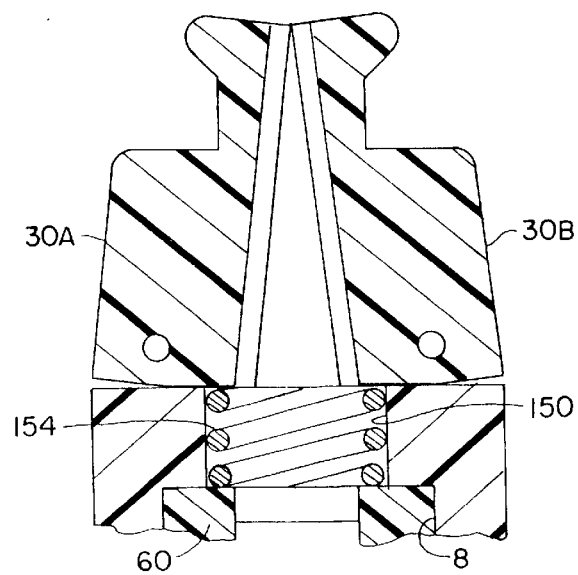
FIG. 21 illustrates a modification of the invention.

It also is appreciated that the device may be modified by replacing the spring members 52, 54A, 54B with a different form of spring. Thus, as shown in FIG. 21, body 2 may be formed with a bore section 150 that is contiguous with bore section 8 and serves to accommodate a compression coil spring 154 that engages jaws 30A and 30B. Spring 154 biases the jaws to open position.

Still other modifications will be obvious to a person skilled in the art from the foregoing description and the drawings.

The invention has a number of other advantages. For one thing, the device betters controls the stability of the anterior chamber of the eye and increases safety by better stabilizing the surgical field because it minimizes significant fluid egress from the wound. Also the need for a relatively tight squeezing of the scleral tissue around the phaco tip is significantly lessened and the likelihood of the so-called "oar locking" phenomenon that may occur with a squeezing incision is minimized.

An additional advantage of the invention is that the port/seal device not only acts to seal off the opening in the above-described device when no instrument is inserted into the new device (or when an instrument is withdrawn), but also forms a seal around the inserted instrument and allows for required maneuvering of the instrument, e.g., properly aligning it with the axis of the device to facilitate insertion, thereby avoiding distortion of the surrounding tissue as the instrument is positioned by the surgeon.

Still other advantages of the invention include (1) better control over wound size, (2) universal adaptability for use with various surgical apparatus; (3) easier insertion and manipulation of instruments with less trauma and thermal damage to surrounding scleral and corneal tissue, including corneal endothelium and Descemet's membrane, (4) a reduction in the amount of infusion fluid required to be supplied to the system for a given surgical procedure, (5) reduced wound leakage, (6) better maintenance of anterior chamber depth during a given eye surgical procedure, (7) a reduction in posterior capsule tears due to better control and more consistent maintenance of the anterior chamber depth, (8) easier insertion of intraocular lens by standardizing the size of the incision and protecting the scleral from tearing during phaco instrument insertion and use, (9) ability to use a smaller phaco tip now that a squeezable outer infusion sleeve is no longer necessary to cover the ultrasound vibrating phaco tip, and (10) obtainment of a more stable postoperative wound due to less trauma. Also it is expected that use of the device will reduce intra-operative and post-operative complications.

With respect to thermal burning, it should be noted that the use of a deformable infusion sleeve around the phaco needle presents a problem in that often the incised tissue tends to pinch the infusion sleeve against the phaco needle, with the result that heat is transmitted from the needle through the wall of the infusion sleeve to the surrounding incised tissue, thus causing thermal burning. That particular problem is overcome by the present invention which utilizes a stiff infusion sleeve that will not distort into heat-transmitting engagement with the phaco tip or needle.

The foregoing all contribute to achieving a safer phacoemulsification procedure and also facilitate other ocular surgery where direct access to the interior of the eye is necessary.

Although the device of the present invention is designed primarily to facilitate successful cataract removal by phacoemulsification, it may be used for other types of ophthalmic surgery (e.g., retinal surgery) and even for other non-ophthalmic surgical procedures, e.g., orthopedic knee operations. Moreover, more than one device made according to this invention may be used in a given surgical procedure. Thus, for example, several such devices may be used for retinal surgery, with each such device being used as a port for different instruments or purposes.

What is claimed is:

1. An instrument port device for use in surgery comprising:
    a housing having a distal end, a proximal end, and an internal longitudinally-extending passageway between said distal and proximal ends through which a surgical instrument may be inserted and withdrawn;
    at least two jaws mounted to said distal end of said housing, said jaws having interior surfaces and exterior surfaces and being mounted for reciprocal movement between a first open position in which said interior surfaces are spaced from one another and a second closed position in which at least a portion of said interior surfaces are engaged with one another; and
    sealing means for providing a fluid seal between said housing and a surgical instrument that is inserted into said passageway.

2. A device according to claim 1 wherein said jaws project outwardly from said distal end of said housing.

3. A device according to claim 1 wherein said sealing means comprises an elastomeric member located within said housing.

4. A device according to claim 3 wherein said elastomeric member is characterized by a self-sealing opening.

5. A device according to claim 3 wherein said sealing means comprises a substantially flat disk-shaped member having a slitted central portion.

6. A device according to claim 1 wherein said sealing means comprises a sealing member having an annular rim portion and a central portion, with said central portion being divided by razor slits into a plurality of wedge-shaped sections.

7. A device according to claim 1 wherein said passageway comprises a first diameter section and a second diameter section, and further including a fluid sealing means disposed in said first diameter section and a spring engaged with said jaws disposed in said second diameter section, said spring acting to bias said jaws to said first open position.

8. A device according to claim 7 wherein said fluid sealing means is adapted to accommodate and form a seal around a surgical instrument that is inserted into said internal passageway.

9. A device according to claim 1 wherein said jaws are pivotally mounted to said housing.

10. A device according to claim 9 wherein said jaws total two in number and are disposed opposite to one another, and further wherein said interior surfaces of said jaws have a concave cross-sectional shape.

11. A device according to claim 9 wherein said jaws are pivotally mounted in slots formed in said distal end of said housing.

12. A device according to claim 1 wherein said exterior surfaces of said jaws define a generally elliptical shape.

13. An instrument according to claim 1 wherein said housing has a slot at its said distal end, and said jaws are mounted in said slot.

14. An instrument according to claim 13 wherein said jaws are pivotally attached to said housing.

15. An instrument according to claim 1 further including spring means attached to said housing in position to bias said jaws to said first open position.

16. An instrument according to claim 13 wherein said jaws have incision-sealing portions that are in the form of an ellipsoid.

17. A device according to claim 1 further including means for biasing said jaws into said first open position.

18. A device according to claim 17 wherein said biasing means comprises a spring mounted within said housing.

19. In combination with a phaco tip comprising a hollow needle having a tip that is surrounded at least in part by an infusion sleeve, a port device that comprises the following:
 a housing having a distal end, a proximal end, and a central internal longitudinally-extending passageway between said distal and proximal ends through which said needle and sleeve may be inserted and withdrawn;
 at least two jaws mounted to said distal end of said housing, said jaws having interior surfaces and exterior surfaces and being mounted for movement between a first open position in which said interior surfaces are spaced from one another and a second closed position in which at least a portion of said interior surfaces are engaged with one another; and
 said exterior surface being characterized by means whereby an exterior force may be applied to said jaws to force them to said second closed position.

20. A combination as called for by claim 19 wherein said infusion sleeve is substantially stiff.

21. A combination as called for by claim 19 wherein said infusion sleeve is substantially rigid.

22. A combination as called for by claim 19 wherein said exterior surfaces of said jaws define a generally elliptical shape.

23. A combination as called for by claim 19 further including a seal member in said housing for closing off said passageway.

24. The combination of a port/seal device for use in surgery and an installation tool for installing said device;
 said port/seal device comprising (1) a housing having a distal end, a proximal end, and an internal passageway extending longitudinally between said distal and proximal ends through which a surgical instrument may be inserted and withdrawn, (2) at least two jaws mounted to and projecting from said distal end of said housing, said jaws having interior surfaces and exterior surfaces and being mounted for movement between a first open position in which said interior surfaces are spaced from one another and a second closed position in which at least a portion of said interior surfaces are engaged with one another, said jaws also having projections whereby an exterior force may be applied to said jaws to force them to said second closed position, said exterior surfaces of said jaws also being shaped so as to make a close fit with an eye incision, and (3) spring means biasing said jaws to said first open position; and
 said installation tool comprising a tubular member having a distal end for receiving said port/seal device, said distal end being sized so as to engage said projections and thereby hold said jaws in said second closed position; and a second member telescopingly mounted in said tubular member for movement between a first retracted position and a second extended position, said first retracted position being such as to permit said port/seal device to be received by said tubular member with its jaws held thereby in said second closed position, and said second extended position being such that in moving thereto said second member pushes said port/seal device outwardly of said tubular member and thereby frees said jaws for movement by said spring means to said second open position.

25. The combination of claim 24 wherein said port/seal device includes a seal member disposed within said housing, said seal member being adapted to (a) prevent leakage of fluid from said housing via said internal passageway and (b) permit a surgical instrument to be inserted into said passageway without any leakage of fluid around said surgical instrument.

26. An instrument port device for use in surgery comprising:
 a housing having a distal end, a proximal end, and an internal longitudinally-extending passageway between said distal and proximal ends through which a surgical instrument may be inserted and withdrawn;
 at least two jaws mounted to said distal end of said housing, said jaws having interior surfaces and exterior surfaces;
 means pivotally mounting said jaws to said housing for reciprocal movement between a first open position in which said interior surfaces are spaced from one another and a second closed position in which at least a portion of said interior surfaces are engaged with one another; and
 sealing means carried by said housing for providing a fluid seal between said housing and a surgical instrument that is inserted into said passageway.

27. An instrument according to claim 26 wherein each of said jaws comprises a body portion and a tissue-engaging incision-penetrating portion.

28. An instrument according to claim 27 wherein said tissue-engaging incision-penetrating portion is an extension of said body portion.

29. An instrument according to claim 28 wherein said tissue-engaging incision-penetrating portion of each jaw is stepped, having a relatively large distal end section and a relatively small proximal end section that is joined to said body portion.

30. An instrument according to claim 29 wherein said relatively large distal end section has outer surfaces that define a triangular configuration.

31. An instrument port device for use in surgery comprising:

a housing having a distal end, a proximal end, and an internal longitudinally-extending passageway between said distal and proximal ends through which a surgical instrument may be inserted and withdrawn;

at least two jaws mounted to said distal end of said housing, said jaws having interior surfaces and exterior surfaces and being mounted for reciprocal movement between a first open position in which said interior surfaces are spaced from one another and a second closed position in which at least a portion of said interior surfaces are engaged with one another, said exterior surfaces being characterized by means whereby an exterior force may be applied to said jaws to force them to said second closed position; and sealing means for providing a fluid seal between said housing and a surgical instrument that is inserted into said passageway.

32. An instrument port device according to claim 30 wherein said sealing means is disposed in said proximal end of said housing.

33. An instrument port device for use in surgery comprising:

a housing having a distal end, a proximal end, and an internal longitudinally-extending passageway between said distal and proximal ends through which a surgical instrument may be inserted and withdrawn;

at least two jaws mounted to said distal end of said housing, said jaws having interior surfaces and exterior surfaces and being mounted for reciprocal movement between a first open position in which said interior surfaces are spaced from one another and a second closed position in which at least a portion of said interior surfaces are engaged with one another;

said exterior surfaces being characterized by means whereby an exterior force may be applied to said jaws to force them to said second closed position; and means for biasing said jaws into said first open position.

34. A device according to claim 33 further including sealing means for providing a fluid seal between said housing and a surgical instrument that is inserted into said passageway.

35. A device according to claim 34 wherein said sealing means comprises an elastomeric member located within said housing, said elastomeric member being characterized by a self-sealing opening.

36. A device according to claim 33 wherein said biasing means comprises a spring mounted within said housing.

37. A device according to claim 36 wherein said biasing means comprises a leaf spring element.

38. A device according to claim 36 wherein said spring is a compression spring that is engaged directly with said jaws.

39. A device according to claim 33 wherein said jaws are pivotally mounted to said housing.

40. A device according to claim 33 wherein said interior surfaces of said jaws are concave.

41. An instrument port device for use in surgery comprising:

a housing having a distal end, a proximal end, and an internal longitudinally-extending passageway between said distal and proximal ends through which a surgical instrument may be inserted and withdrawn;

at least two jaws having interior surfaces and exterior surfaces;

means mounting said jaws to said distal end of said housing so that said jaws are movable bidirectionally in their entirety between a first open position in which said interior surfaces are spaced from one another and a second closed position in which at least a portion of said interior surfaces are engaged with one another; and said interior surfaces being concave and said exterior surfaces being characterized by means whereby an exterior force may be applied to said jaws to force them to said second closed position.

42. An instrument port device according to claim 26 wherein said jaws have incision-sealing portions that are in the form of an ellipsoid.

* * * * *